(12) United States Patent
Heavener et al.

(10) Patent No.: US 12,016,600 B2
(45) Date of Patent: Jun. 25, 2024

(54) ORTHOPEDIC COMPRESSION PLATE AND METHOD OF SURGERY

(71) Applicant: ORTHOHELIX SURGICAL DESIGNS, INC., Bloomington, MN (US)

(72) Inventors: Jackson R. Heavener, Warsaw, IN (US); Jeffrey Johnson, Chesterfield, MO (US); David B. Kay, Akron, OH (US)

(73) Assignee: ORTHOHELIX SURGICAL DESIGNS, INC., Bloomington, MN (US)

( * ) Notice: Subject to any disclaimer, the term of this patent is extended or adjusted under 35 U.S.C. 154(b) by 114 days.

(21) Appl. No.: 17/714,308

(22) Filed: Apr. 6, 2022

(65) Prior Publication Data

US 2022/0226029 A1    Jul. 21, 2022

Related U.S. Application Data

(60) Continuation of application No. 16/251,891, filed on Jan. 18, 2019, now Pat. No. 11,317,952, which is a continuation of application No. 15/445,242, filed on Feb. 28, 2017, now Pat. No. 10,213,236, which is a continuation of application No. 14/713,401, filed on May 15, 2015, now abandoned, which is a division of application No. 13/728,532, filed on Dec. 27, 2012, now Pat. No. 9,060,822, which is a
(Continued)

(51) Int. Cl.
A61B 17/80    (2006.01)
A61B 17/86    (2006.01)

(52) U.S. Cl.
CPC ...... *A61B 17/8014* (2013.01); *A61B 17/8057* (2013.01); *A61B 17/8061* (2013.01); *A61B 17/8605* (2013.01); *A61B 17/8095* (2013.01)

(58) Field of Classification Search
CPC . A61B 17/8605; A61B 17/8614; A61B 17/80; A61B 17/8061
USPC ...... 606/281, 282, 297; 623/21.19
See application file for complete search history.

(56) References Cited

U.S. PATENT DOCUMENTS

| | | |
|---|---|---|
| 3,489,143 A | 1/1970 | Halloran |
| 4,493,317 A | 1/1985 | Klaue |
| 5,534,027 A | 7/1996 | Hodorek |

(Continued)

FOREIGN PATENT DOCUMENTS

| | | |
|---|---|---|
| WO | 9708999 A1 | 3/1997 |

OTHER PUBLICATIONS

European Search Report issued for European patent application No. 12862889.8, Nov. 23, 2015, 8 pages.
(Continued)

*Primary Examiner* — David W Bates
(74) *Attorney, Agent, or Firm* — DUANE MORRIS LLP

(57) ABSTRACT

An orthopedic plate has a first end including a locking screw hole that receives a locking screw and spaced from that hole is a closed compression housing that extends from the bone-facing side of the plate and which receives a compression screw that forms an angle of from about 10° to about 70° with a longitudinal axis of the plate. The compression housing is not located on the medial line of the plate, but is peripheral to the medial line, either in the longitudinal or the medial direction of the plate.

9 Claims, 10 Drawing Sheets

Related U.S. Application Data continuation-in-part of application No. 13/372,902, filed on Feb. 14, 2012, now Pat. No. 9,005,255.

(60) Provisional application No. 61/580,680, filed on Dec. 28, 2011.

(56) References Cited

U.S. PATENT DOCUMENTS

| | | | |
|---|---|---|---|
| 5,591,169 A | 1/1997 | Benoist | |
| 5,607,428 A * | 3/1997 | Lin | A61B 17/8047 606/287 |
| 5,667,510 A | 9/1997 | Combs | |
| 5,693,055 A | 12/1997 | Zahiri | |
| 6,623,486 B1 * | 9/2003 | Weaver | A61B 17/8625 606/291 |
| 7,128,744 B2 | 10/2006 | Weaver et al. | |
| 7,648,508 B2 * | 1/2010 | Lutz | A61B 17/842 606/86 R |
| 7,717,945 B2 | 5/2010 | Jensen et al. | |
| 8,182,484 B2 | 5/2012 | Grant et al. | |
| 8,187,276 B1 | 5/2012 | Zahiri | |
| 8,231,625 B2 | 7/2012 | Graham et al. | |
| 8,556,946 B2 | 10/2013 | Prandi et al. | |
| 8,617,224 B2 | 12/2013 | Kozak et al. | |
| 8,740,915 B2 | 6/2014 | Niederberger et al. | |
| 8,852,246 B2 | 10/2014 | Hansson | |
| 8,858,602 B2 | 10/2014 | Weiner et al. | |
| 9,005,255 B2 | 4/2015 | Lewis et al. | |
| 9,907,588 B2 | 3/2018 | Parekh et al. | |
| 2002/0045896 A1 | 4/2002 | Michelson | |
| 2003/0040748 A1 | 2/2003 | Aikins | |
| 2003/0060827 A1 | 3/2003 | Coughln | |
| 2004/0143266 A1 | 7/2004 | Kozak et al. | |
| 2005/0010226 A1 * | 1/2005 | Grady | A61B 17/809 606/291 |
| 2005/0171544 A1 | 8/2005 | Falkner | |
| 2007/0173843 A1 * | 7/2007 | Matityahu | A61B 17/80 606/281 |
| 2008/0015593 A1 | 1/2008 | Pfefferle et al. | |
| 2009/0036931 A1 | 2/2009 | Pech et al. | |
| 2009/0076554 A1 | 3/2009 | Huebner et al. | |
| 2009/0210010 A1 | 8/2009 | Strnad et al. | |
| 2009/0210011 A1 | 8/2009 | Den Hartog et al. | |
| 2010/0125300 A1 | 5/2010 | Blitz et al. | |
| 2010/0274293 A1 * | 10/2010 | Terrill | A61B 17/8061 606/286 |
| 2011/0009866 A1 | 1/2011 | Johnson et al. | |
| 2011/0098757 A1 | 4/2011 | Schelling | |
| 2011/0295324 A1 | 12/2011 | Donley et al. | |
| 2012/0303033 A1 | 11/2012 | Weiner et al. | |
| 2014/0148859 A1 | 5/2014 | Taylor et al. | |

OTHER PUBLICATIONS

Supplementary European Search Report issued for European patent application No. 12746929, filed Nov. 12, 2015, 3 pages.

Extended European Search Report issued for European patent application No. 17158160.6, Apr. 12, 2017, 8 pages.

* cited by examiner

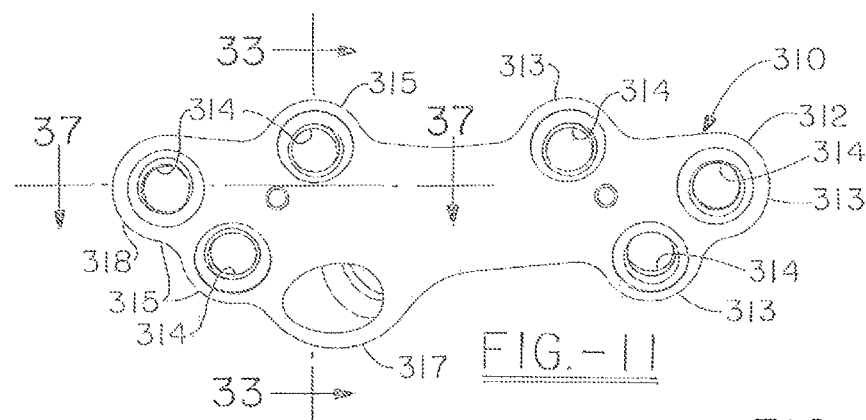
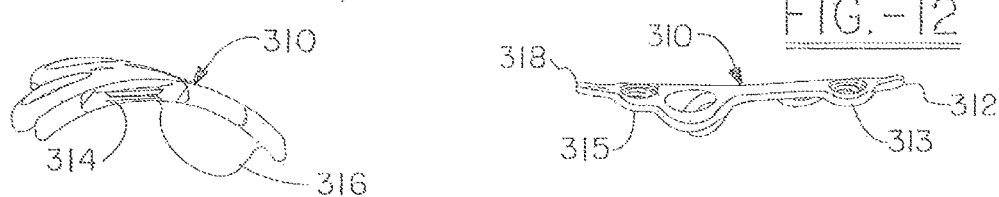
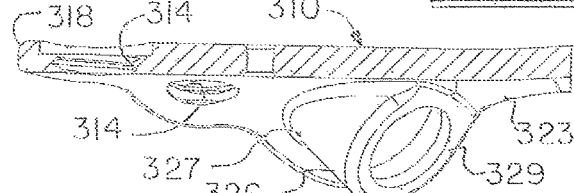
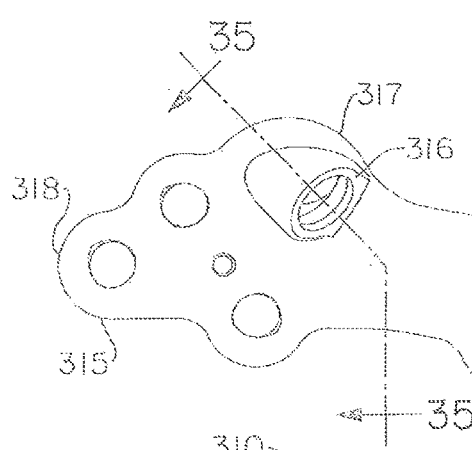
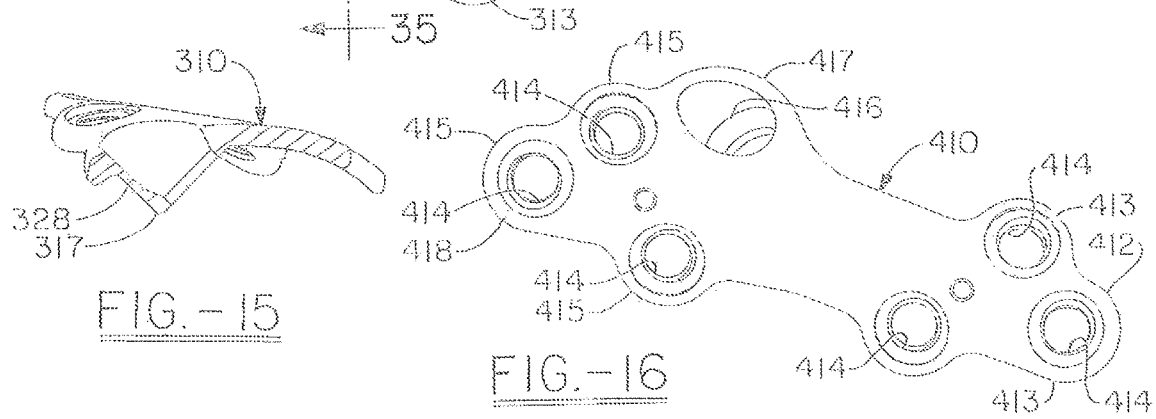

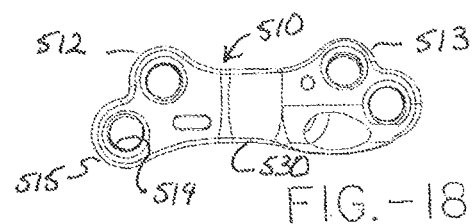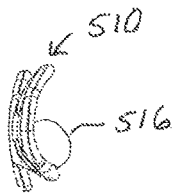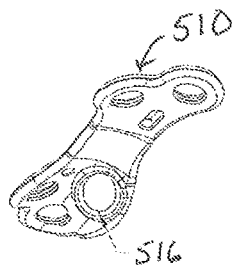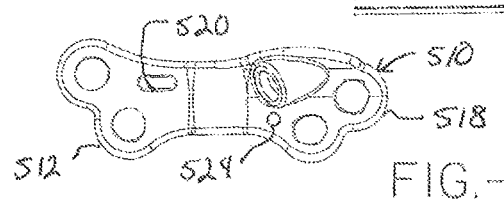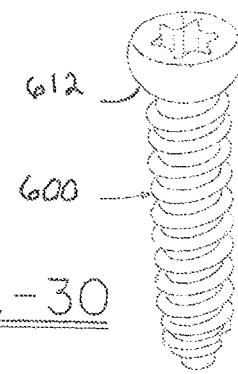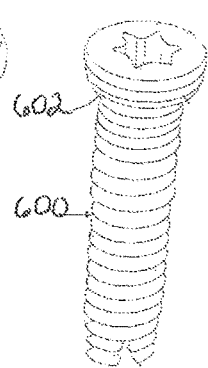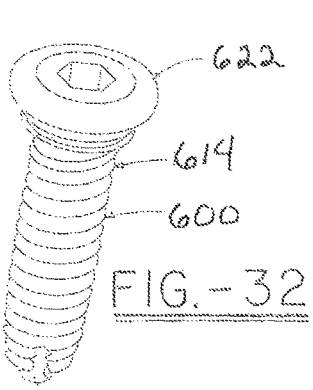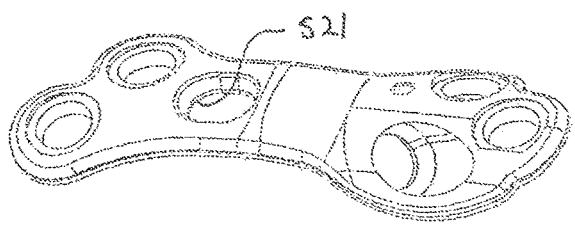

ORTHOPEDIC COMPRESSION PLATE AND METHOD OF SURGERY

CROSS REFERENCE

This application is a continuation application of pending U.S. patent application Ser. No. 16/251,891, filed Jan. 18, 2019 which is a continuation of U.S. Pat. No. 10,213,236, issued Feb. 26, 2019, which is a continuation of abandoned U.S. patent application Ser. No. 14/713,401, filed May 15, 2015, which is a divisional of U.S. Pat. No. 9,060,822, issued Jun. 23, 2015, which is a CIP of U.S. Pat. No. 9,005,255, issued Apr. 14, 2015 which claims the benefit of priority under 35 U.S.C. § 119 of U.S. Provisional Application Ser. No. 61/580,680, filed on Dec. 28, 2011, herein fully incorporated by reference.

FIELD OF THE INVENTION

The present invention relates to an orthopedic plate, which is configured to increase compression at a bone interface, in particular to stabilize bones or bone fragments relative to each other such as to cause fusion. Specific embodiments and methods of fixation are presented for fixation of the bones of the foot including, for example, stabilization of a fracture, dislocation or reconstruction of a deformity such as use in osteotomies and bunionectomies. The invention also applies to fusion procedures in other areas of the body, including the wrist or hand. The plate has a compression structure located generally peripherally to the mass of the plate, which receives a screw that acts as an inter-fragmentary screw while the plate augments the stabilization and compression that is achieved by the screw. The plate is provided with an elongated structure or body that allows the plate to be fixed to the bone fragments while the compression is achieved using the screw. In a further embodiment, the invention relates to a system of plates for use in lapidus procedures and to a method of correction of bunions using the present invention.

BACKGROUND OF THE INVENTION

The feet and the hands both include numerous bones and joints that cooperate together to define quintessential human movement. They are sophisticated, delicate and altogether elegant in function and design. Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body. The hand forms a cognate to the foot with 27 bones within the hand and wrist. There are eight small bones within the wrist called the carpals, which join with the radius and the ulna to form the wrist joint. The carpals connect with the five metacarpals to form the palm of the hand, which terminate in the rays (i.e., the thumb and fingers) formed by the phalanges. The three phalanges in each finger are separated by two joints, called interphalangeal joints (IP joints). The one closest to the MCP joint (knuckle) is called the proximal IP joint (PIP joint). The joint near the end of the finger is called the distal IP joint (DIP joint). The thumb only has one IP joint between the two thumb phalanges. The IP joints of the digits also work like hinges when you bend and straighten your fingers and thumb.

Similarly, the forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The forefoot balances pressure on the ball of the foot and bears a substantial amount of the body weight. The first metatarsal forms a joint at the mid-foot with the cuneiform. This joint is referred to as the MTG joint or metatarsocuneiform joint. In the native position, the first metarsal is relatively parallel to the second metatarsal. When bunions are formed, the first metatarsal becomes displaced at an angle relative to the second metatarsal, and often in response, the big toe subluxates.

The bones of the midfoot from medial to lateral are the 1st through 3rd cuneiform, the cuboid, and the crescent shaped navicular bone posterior to the cuneiforms, which also forms a joint with the talus that forms the basis for the ankle joint at the hinged intersection of the tibia, the fibula, and the foot. The five tarsal bones of the midfoot act together form a lateral arch and a longitudinal arch, which help to absorb shock. The plantar fascia (arch ligament) underlays the bones of the midfoot and along with muscles, forms a connection between the forefoot and the hindfoot. The toes and their associated midfoot bones form the first through fifth rays beginning with the great toe as the first ray. The bones which form the palmate portion of the hand are: the scaphoid, the lunate, the triquetrum, the pisiform, the trapezium, the trapezoid, the capitate, and the hamate, which act in concert to allow the opposition of the thumb with each of the fingers and to permit the uniquely human ability to manipulate objects.

The hindfoot is composed of three joints (subtalar, calcaneocuboid & talonavicular) and links the midfoot to the ankle. The heel bone (or "calcaneus") projects posteriorly to the talus and forms a lever arm to activate the hinged action of the foot so as to allow propulsion of the entire body from this joint. The calcaneus is joined to the talus at the subtalar joint. The mid-foot is often the subject of trauma, such as results from falls, vehicle crashes and dropped objects. These accidents often result in severe fractures and/or dislocations. In addition, there are several conditions which result from congenital deformation or which arise as a result of repeated use type injuries. Surgical intervention that includes surgical sectioning of bone or an "osteotomy" is often used to restructure the bones asa treatment for such conditions, for example, the bunionectomy. The present invention is likewise useful for conditions of the hand that result from prior trauma, surgical intervention or defects from birth or that develop with age (such as rheumatoid arthritis).

Examples of some of the other procedures with which the present invention could be used include hallus valgus and hallus rigidus corrections, as well as lapidus surgeries. Other applications, which could use the present invention, include first and fifth metatarsal chevrons, translational osteotomies, closing wedge osteotomies, pediatric femoral osteotomies, metacarpal and calcaneal rotational osteotomies, intrarticular osteotomies and hand and wrist realignment osteotomies. Specific surgical techniques are discussed for the use of an embodiment of the invention designed for use in bunionectomies specifically involving the MTP and MTC joints.

Typical surgical treatment of the foot or hand re-establishes a normal anatomy while the fractured bones mend. In some cases, fusion of a joint may be necessary, for example, where arthritis arises in a patient due touse injuries, poor bone or prior unsuccessful surgeries. One current surgical treatment of these conditions requires that pins, wires and/or screws be inserted to stabilize the bones and joints and hold them in place until healing is complete. For example, a pin or interfragmentary screw may be introduced medially into the internal cuneiform and through the base of the first and/or second metatarsal bone. While the use of k-wires, pins, and screws may provide acceptable results for younger and more plastic patients, these methods of fixation are not always satisfactory, in particular in cases of early weight-bearing on the operative joint, which can result in secondary issues such as elevated metatarsal, plastic deformation, or lesser metatarsal overload.

The present invention combines the advantages of the prior art screw/pin fusion methods with the advantages of a plate, and allows the surgeon the option of using an inter-fragmentary or fusion compression screw in a procedure that also incorporates a plate and thus provides the advantages for stress shielding and force loading or balancing that permits earlier weight bearing. Templates are provided which facilitate the operative procedure, including alignment holes for the positioning of guide wires which can remain in position during placement of the plate, counter-boring the surgical site to accommodate the compression screw housing and placement of the "inter-fragmentary" or compression screw. Further, the plate includes elongated wire and/or screw holes that allow for the compression and attendant relative bone movement during the surgery by the engagement of the compression screw. The compression screw or screws are placed in the plate so as to minimize the possibility of interference with the guide wires and plate screws.

The openings in the plate for the compression screws are provided in a peripheral, and/or distal portion of the plate, and further for some applications are displaced from and do not lie on the long axis of the plate body, but are offset from by means of a longitudinal curve in a extended or tail portion of the plate which receives the screw or by providing a peripheral tab that curves inward so as to wrap the axis. This allows a placement of the compression screw that exerts a force on a diagonal to the long axis of the plate (i.e. a compound force relative to the plate). Further, in one embodiment, a compression housing or "pocket" is provided which projects below the bone-facing surface of the plate, which includes a slotted opening for the compression screw. Thus, the screw can be angled with a single degree of freedom (i.e. linearly) with respect to the axis of the compression screw hole in the housing.

Finally, in a plate system in accordance with the present invention, a surgical tray is provided with a series of plates that include a varying degree of offset to accommodate the correction for a varying degree of anatomical deformity in a lapidus procedure. Preferably this system provides for a left and right set of plates, each set optionally including a first plate that has a compression slot rather than a shrouded compression housing, a "neutral" plate having a compression housing and a 3.5° offset between the posterior and anterior end of the plate, a 4° plate that has a total offset of 7.5°, a 8° plate that has a total offset of 11.5° (all angles being expressed at +/−0.5°) and a medial column plate that is designed to provide for additional fixation of the first ray. At a minimum, the sets include the first plate which is considered "neutral" (and has an offset of 2.5°-4.5°), the second plate which has an additional offset of 2° to 5° (for a total of 4.5°-9.5°) and a third plate has an additional offset of 6° to 10° (for a total of 10° to 20°). The system provides for at least these three plates available during a surgery in a single tray, and additionally the system provides for a left set and a right set of implants, for a total of at least six plates available to the operating surgeon. Optionally, the system may also include a non-pocket plate that has a double tabbed end and an opposing tri-lobed end with the intermediate lobe including a compression slot, and the system may include a medial column plate that has a series of threaded medial tabs for locking screws and at one end a lobe that has a terminal compression slots to achieve compression toward the other end of the plate, and the other end of the plate has a middle compression slot which acts to achieve compression towards the middle of the plate.

SUMMARY OF THE INVENTION

In accordance with the present invention an orthopedic plate is provided that achieves improved compression through the use of a screw that is situated with its axis obliquely to the spine of the plate (i.e. to the longitudinal axis in the plane of the plate taken at the opening of the compression opening of the plate). The term "spine" of the plate is used to mean a line or curve that is generally medial to the mass of the plate, taking into account that the plates of the invention are somewhat more long than wide, but are amorphous in profile, and have end sections that are may be asymmetrically lobed or tabbed with semi-circular conjoined tabs including screw holes that can have internal threads for locking screws.

Preferably, the compression screw is received in a housing or pocket which includes an opening in the top surface of the plate and a shroud which extends fromthe bottom surface of the plate so as to define a pocket on the bottom of the plate that captures the screw at a variable orientation. The housing extends through the plate to accommodate the entire diameter of the head of the screw (i.e. so that the head of the screw does not project significantly or at all beyond the top of the plate when the screw is fully implanted within the plate). Thus, the screw head does not project beyond the top surface of the plate when the screw is fully seated in the housing. (By "top" it is meant herein the exterior facing surface, which is opposite through the thickness of the plate from the bone-facing surface, of the plate when the plate is in position on the bone. It is understood that the orientation relative to the ground is dependent on the orientation of the plate in space, and therefore that is not relevant in determining what is "top" in this case). The housing also includes an opening on the bottom of the plate through which the screw extends and which is smaller than the diameter of the screw head so as to capture the screw in the housing. Also the housing is slightly larger than the bottom opening so that the convexly rounded screw head has some play in the pocket to allow some freedom of angulation (i.e. about 5 to about 30°, preferably about 10 to about 20°) of conical or modified conical rotational freedom of the screw relative to the housing axis (as measured from the groove formed through the compression opening.) In a further embodiment, the opening is elongated or is a slot, which allows the screw to be placed at a linear variable angle (that is a restricted portion of the conical angulation) relative to the housing, where the amount of angulation is about +/−120, preferably +/−10°, and more preferably +/−6° of linear freedom relative to the axis of the housing. The angle of the axis of the oblique screw is from about 10° to about 70°, more specifically about 25° to about 60° and most specifically about 35° to about 55° degrees to a longitudinal axis of the plate which dissects the compression opening on the plate (i.e. the "spine of the plate"). A compressive force is applied to the bone or bone fragments by the plate as the oblique screw is screwed tighter and the screwhead compresses into an increased fit with the pocket, and in particular with the pocket bottom opening. This draws that bone segment into which the compression screw is screwed, toward the locking screw or screw in the other end of the plate and accordingly into compression with the bone segment into which the screws associated with the other end of the plate, are screwed.

In a first embodiment, of the plate, an application specific configuration is illustrated as a MTP plate, which is intended to span the MTP joint. In a first version of the MTP plate of the present invention, the plate outline has (again "consists essentially of") a first end with two lateral tabs on either side of a middle tab, and a second end with two lateral tabs and no intermediate tab. Each of these tabs is provided with a threaded screw hole that receives a threaded locking screw. The end with the two tabs, also includes a compression housing as previously described that accepts a screw which extends toward the first end of the plate with its axis at an oblique angle of about 5° to about 40°, more preferably about 10° to about 30°, and most preferably about 15° to about 25° with respect to the longitudinal axis of the plate. Further, the plate has an angle of up to about 10° (and preferably about 5°) for dorsiflexion and an angle up to about 10° for valgus. The bottom surface of the plate is radiused. This allows the plate to be in snug contact with the bone. This plate is also provided in a second version which differs from the first in that the second end does include three tabs similar to the first end, an the compression housing is located at at an oblique angle of about 5° to about 40°, more preferably about 10° to about 30°, and most preferably about 15° to about 25° to the lateral side of the plate and intermediate along the longitudinal axis to the tabs, and further houses a screw hole that defines an axis at an angle of about 55°, /−about 15°, preferably about 10°, and most preferably about 5° to a line perpendicular to the plate surface at a point along the plate longitudinal axis. The compression housing is similar in concept to the previously described compression housing, but in this case, has a round footprint describing at least a portion of a circle, and preferably is substantially a portion of a circle, with a leading edge that is linear. Once again, the housing has an internal recess that houses the compression screw and which has a narrowed opening, that is smaller than an associated screw head so as to capture and retain the screw, but which allow for conical rotation in the compression housing.

A third embodiment of the plate is intended for use in lapidus procedures which are also used to correct bunions, but by realigning the metatarsal relative to the rear joint with the cuneiform. Lapidus procedures in accordance with the present invention have several advantages over past procedures, including earlier post operative weight bearing, inhibition of elastic deformation, preservation of the function of the MTP joint, realignment of the big toe, better outcomes in the event of mal-union or non-union, and better rear-foot alignment.

In the plate system in accordance with this embodiment, the plate has an even more complex footprint with the posterior end (i.e. toward the heel end of the plate) of the plate including a double tabbed end with each tab including a threaded locking screw hole, and where the inferior tab proceeds (i.e, is rearwards of) the superior tab in the posterior direction. The anterior end of the plate includes a tri-lobed outline in which the central lobe and the superior lobe or tab include internally threaded locking screw holes, and the third lobe or tab which is less distinct than the other two lobes and is curved inward and downward toward the bone-facing surface. This lobe includes a shroud, housing or pocket which projects below the plate as the previously described screw housings, and which receives a screw that projects posteriorly and dorsally to apply compression across the MTC (metatarsocuneiform) joint. This embodiment of the invention differs from the first embodiment in that the compression screw housing is provided in a location that does not lie on the longitudinal axis, and more preferably is located in a peripheral (both longitudinally and medially) portion of the plate which accepts a screw so as to pull a compressive force diagonally across the body of the plate in opposition to the plate screws that hole the plate in position relative to the bone segments. Thus, the screw applies a compound force (i.e. having force components in the direction of the longitudinal axis and transverse to it) so that this plate presents the advantages of the prior art interfragmentary screws which tend to be placed in this position, combined with the additional stability and weight bearing ability of a plate which wraps the bone and creates a construct with the bone that is aligned to stabilize with the bone axes.

The invention also relates to a novel surgical procedure, which is a bunionectomy that involves the use of the bunionectomy plate of the present invention, as well as to a lapidus procedure which utilizes the plate in accordance with the invention where a template is placed along with guide wires, the bone is reamed to receive the compression screw pocket, the template is slid off the guide wires and the plate is slid on, all the time maintaining the established alignment of the bones with the guide wires. The distal plate screws are place in the anterior end of the plate, a guide wire is placed through the joint, and a cannulated screw is placed in the compression pocket across the joint. Since the plate is provided with slot or slots in opposition to the compression pocket, and the template is provided with guide wire holes spaced appropriately to account for the compression achieved with the screw, the guide wires move in the slots in the plate to account for the compression achieved by the compression screw. The guide wires can be removed, the posterior screws are implanted, and the wound can be closed. The plate and template system allow the security of the guide wire used for the interfragmentary compression, and the screws allow for multiplanar fixation, while inhibiting the possibility of screw interference. Alternatively to the guide wire slots, the plate can include slotted screw holes and the plate can be attached to bone using these slotted holes prior to the tightening of the compression screw where the screws slide in the slot to account for a change in the relative position in the plate as compression is achieved across the joint or between the bone fragments.

BRIEF DESCRIPTION OF THE DRAWINGS

FIG. 11 is a top view of a second version of the embodiment of the plate shown in FIG. 1;

FIG. 12 is a first side view of the plate shown in FIG. 11;

FIG. 13 is a cross-section of the plate shown in FIG. 11 taken along line 13-13;

FIG. 14 is a bottom view of the plate shown in FIG. 11;

FIG. 15 is a cross-section of the plate shown in FIG. 11 taken at line 15-15;

FIG. 16 is a top view of a left version of the embodiment of the plate shown in FIG. 11;

FIG. 17 is a detail in cross section of the plate shown in FIG. 11;

FIG. 18 is a top view of a third embodiment of the orthopedic compression plate in accordance with the present invention;

FIG. 19 is a first side view of the orthopedic plate of FIG. 18;

FIG. 20 is a bottom view of the orthopedic plate of FIG. 18;

FIG. 21 is a first end view of the plate of FIG. 18;

FIG. 22 is a second end view of the plate shown in FIG. 18;

FIG. 23 is an end and bottom view of the plate of FIG. 18 which illustrates the compression screw opening;

FIG. 30 is a side view of a non-locking screw that can be used with the invention;

FIG. 31 is a side view of a locking screw that can be used with the invention;

FIG. 32 is a side view of a variable locking assembly that can be used with the invention;

FIG. 34 is an alternative embodiment of the MTC plate of FIG. 18.

DETAILED DESCRIPTION OF THE INVENTION

Figure 1:
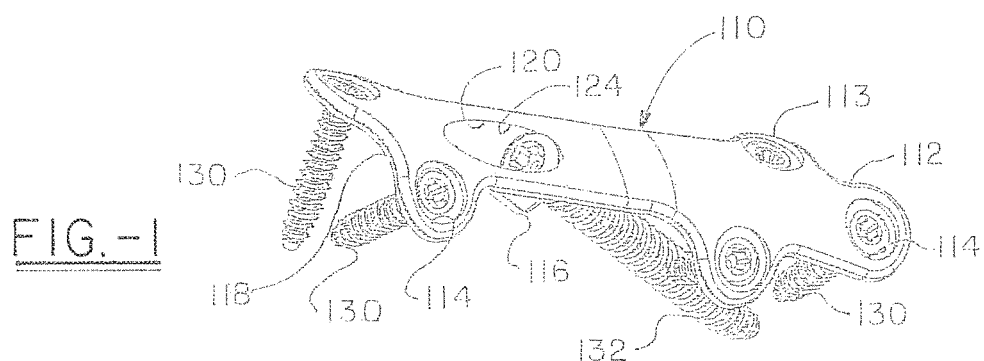
FIG. 1 is a top perspective view of a first embodiment of the orthopedic compression plate in accordance with the present invention.
Figure 2:
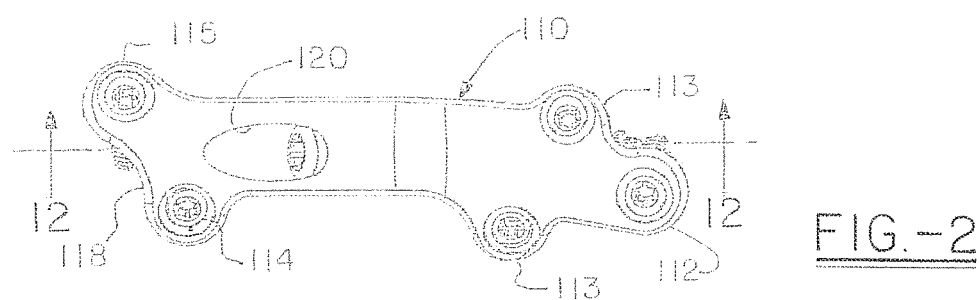
FIG. 2 is a top view of the orthopedic plate of FIG. 1.
Figure 3:
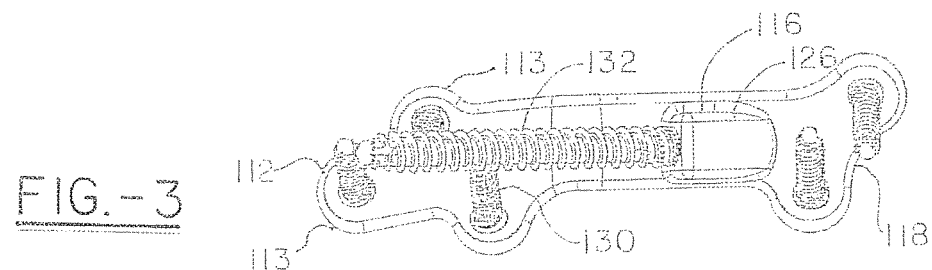
FIG. 3 is a bottom view of the orthopedic plate of FIG. 1.
Figure 4:
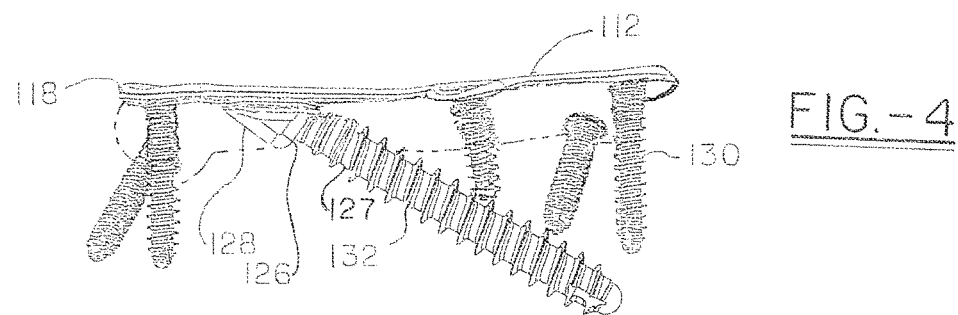
FIG. 4 is a side and bottom perspective view of the plate of FIG. 1.
Figure 5:
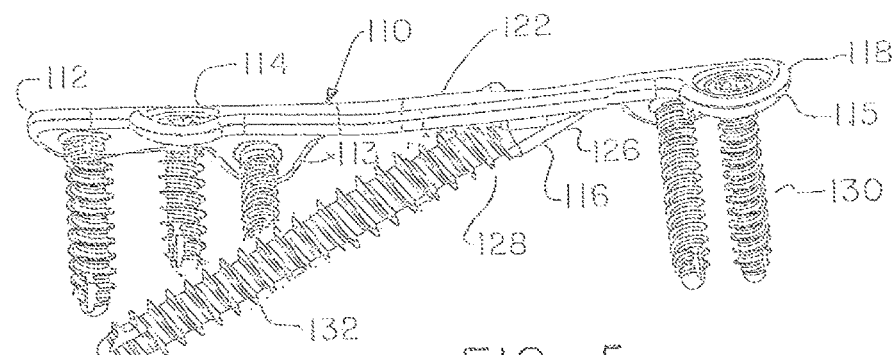
FIG. 5 is a first side view of the plate shown in FIG. 1.
Figure 6:
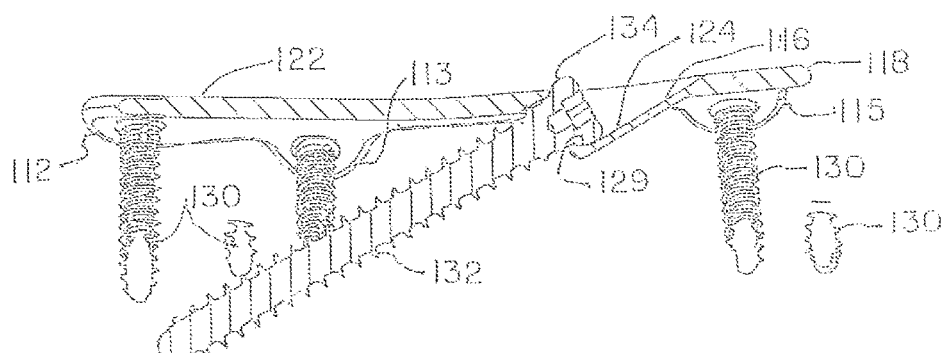
FIG. 6 is a first cross-sectional view of the plate shown in FIG. 2, taken along line 6-6.
Figure 7:
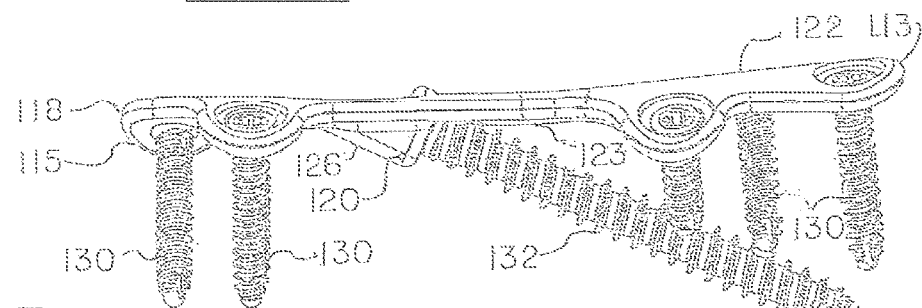
FIG. 7 is a side view taken from the other side of the plate shown in FIG. 1.
Figure 8:
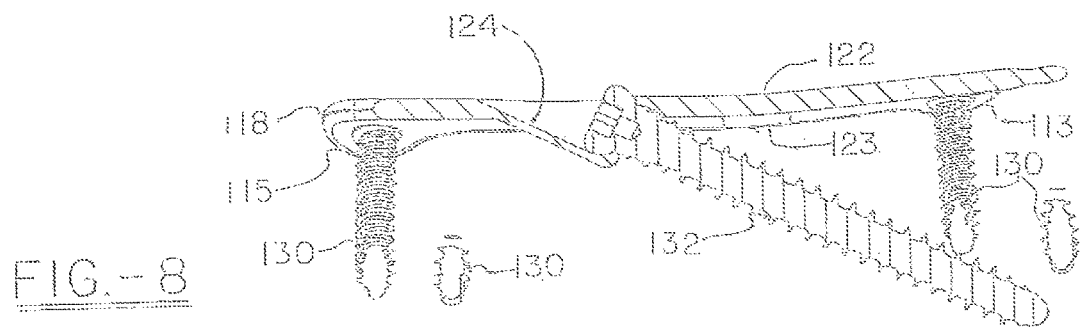
FIG. 8 is a second cross-sectional view of the plate shown in FIG. 2, taken along line 6-6 and looking in the opposite direction from FIG. 6.
Figure 9:
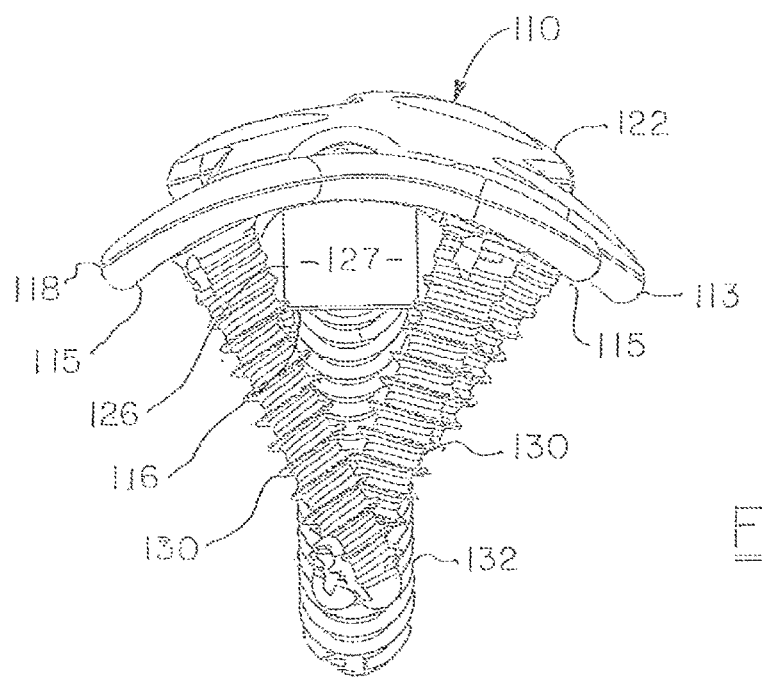
FIG. 9 is a left end view of the plate shown in FIG. 1.
Figure 10:
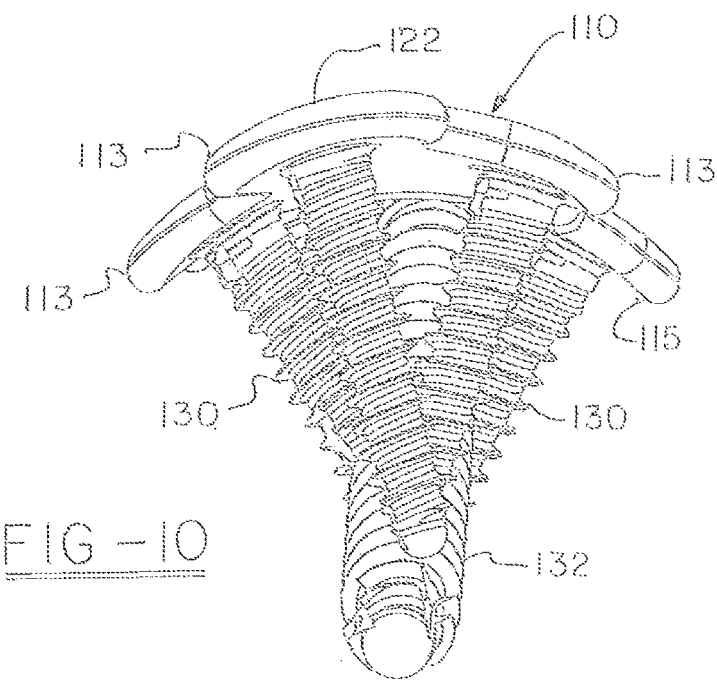
FIG. 10 is a right end view of the plate shown in FIG. 1.
Figure 24:
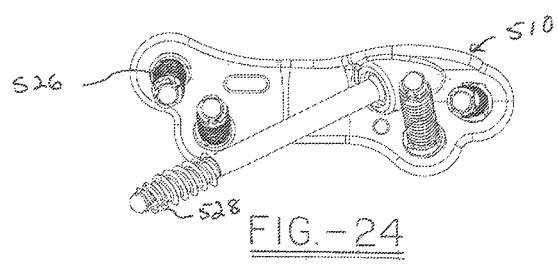
FIG. 24 is a bottom view of the orthopedic plate of FIG. 18 including associated screws to form a plate assembly.
Figure 27:
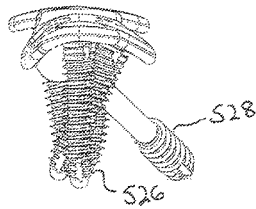
FIG. 27 is a first end view of the plate assembly of FIG. 24.
Figure 25:
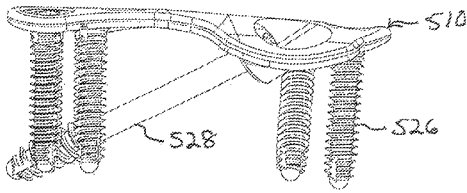
FIG. 25 is a first side view of the orthopedic plate assembly of FIG. 24.
Figure 28:
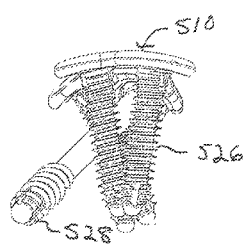
FIG. 28 is a second end view of the plate assembly shown in FIG. 24.
Figure 26:
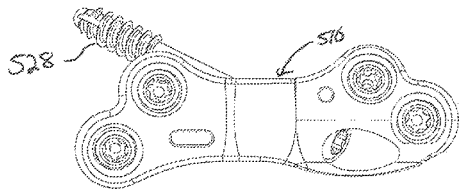
FIG. 26 is a top view of the orthopedic plate assembly of FIG. 24.

FIGS. 1-10 show a first version of plate for use in the MTP joint, the junction of the head of the first metatarsal and the proximal phalange of the first ray (i.e. the great toe) at the first metatarsophalangeal joint. The plate used in fixation (i.e. for fusion) of the bones of the first MTP joint, and is thus termed an MTP plate. The plate 110 has a first end 112 which is tri-lobed, or has three rounds tabs 113, of just appropriate size to form mounting rings for threaded locking holes 114 which receive the locking screws having an externally threaded locking head. The tabs include a rounded portion for example large enough to accommodate an opening for a screw hole, and contiguous material that holds the rounded projection to the general plate body. The tabs are longitudinally offset from each other, and angled inward toward the medial axis of the plate to improve the purchase in the plate, and inhibit backout. The other end 118 of the plate 110 includes two laterally and longitudinally offset tabs 115 which are also just of appropriate size to form mounting rings for threaded lockingholes 114 which receive threaded locking screws 130. The second end 118 of the plate includes a compression housing similar 116.

The compression housing 116 includes an opening 120 in the top surface 122 of the plate. The opening 120 is ovoid, with a width that wide enough to accept the compression screw 132 that is received in the opening 120. The compression screw is of slightly greater diameter and of greater length than the locking screws. The opening 120 angles into the top surface 122 of the plate 110 so as to form a groove 124 that accommodates and guides the screw 132 and a mating driver as the screw is screwed into the bone below the plate. On the bottom surface 123 of the plate 110 there is a shroud 126, which has a rectangular flat rear surface 127 joined to flat side walls 128. The term "shroud" as used herein means that the housing creates a "pocket" of enclosed space for the compression screw head, which is closed to the bone surface and in which the structure that defines the enclosed space is connected at each side to the bottom of the plate. This reinforces the housing structure, helps to create additional compression and closes the housing from the possibility of tissue interference or in-growth. The "housing" comprises a more complete structure than a flat solid rib which projects from the bottom surface of the plate and includes a screw hole (threaded or not). The shroud 126 includes a lower opening 129 which is circular, and which is large enough to allow the major diameter of the screw to pass through, but which is smaller than the diameter of the rounded portion 134 of the head of the screw 132. The compression housing 126 accepts a screw 132 which extends toward the first end 112 of the plate with its axis at an oblique angle of about 5° to about 40°, more preferably about 10° to about 30°, and most preferably about 15° to about 25° with respect to the longitudinal spine of the plate. Further, the plate has an angle of up to about 10° (and preferably about 5°) for dorsiflexion and an angle up to about 100 for valgus. The bottom surface of the plate is radiused at a constant curve.

FIGS. 11-17 illustrate a second embodiment, i.e. the MPT plate 310, of the present invention. In this version both the first and the second ends 312, 318 includes three tabs 313, 315 and locking holes 314 within each tab. The plate 310 continues to have the same angles for dorsiflexion and for valgus. In the first end, in which an axis can be defined along the medial axis of the plate to the mid-line, and dividing the terminal most screw hole in half, the second tab hole forms an angle of about 25° to the long axis and the screw hole has an angle of about 21°+/−8°, preferably +/−about 5°, and most preferably about 2° to the screw axis of the terminal most hole, while the screw hole in the third tab has an angle of about 18°+/−8°, preferably +/−about 5°, and most preferably about 2° to the screw axis of the terminal most hole, with a preferred difference of about 3°. The geometry of the opposite end of the plate mirrors the first end, with the exception that the second end further includes a tab 317 for a compression shroud 316 which extends from the bottom surface of the plate and intermediate to the second tab and has a screw housing that extends from the bottom of the plate at an angle of about 55°+/−about 10°, preferably about 8°, and most preferably about 5° relative to the screw hole axis of the terminal most screw hole. The housing has a cylindrical configuration, which intersects the plate at a linear edge. The housing has a narrowed opening that acts to capture a screw housed in the housing but which allows conical rotation in the housing. The inside wall of the housing narrows at an angle of 40° relative to the axis of the housing. The housing 316 has a narrowed opening that acts to capture a screw housed in the housing but which allows conical rotation in the housing. The inside wall of the housing narrows at an angle of 40° relative to the axis of the housing. On the bottom surface 323 of the plate 310 there is a shroud 316, which has a rear surface 327 joined to side walls 328. The shroud 316 includes a lower opening 329 which is circular, and which is large enough to allow the major diameter of the screw to pass through, but which is smaller than the diameter of the rounded portion 234 of the head of the screw 232. FIG. 16 shows right plate MPT plate 410 which is a mirror image of the left MPT plate shown in FIG. 10. Once again, both the first and the second ends 412, 418 includes three tabs and locking holes 414 within each tab and the second end also includes a tab 417 for a compression shroud 416 which extends from the bottom surface of the plate. The plate continues to have the same angles for dorsiflexion and for valgus. The geometry of the opposite end of the plate mirrors the first end, with the exception that the second end further includes a fourth tab intermediate to the second tab and has a screw housing that extends from the bottom of the plate at an angle of about 55°+/−about 10°, preferably about 8°, and most preferably about 5° relative to the screw hole axis of the terminal most screw hole. The housing has a cylindrical configuration, which intersects the plate at a linear edge.

FIGS. 18-28 illustrate a third embodiment of the invention which is a lapidus plate and assembly designed for use in lapidus procedures. This plate 510 has a first end 512 and a second end 518, where the first end includes two tabs 515, each having internally threaded locking screw holes 514. A second end 518 has three conjoined tabs or lobes 515 two of which include internally threaded locking screw holes 514. The third lobe includes a compression housing 516 that projects into the plate so as to provide a seat for a compression screw and a structure that will also contribute to this compression in the bone. Once again, this compression housing is a peripheral compression housing that is not located on the spine or longitudinal axis of the plate, and the screw located in this housing does not act to apply a force substantially solely in the direction of the longitudinal axis or along the spine of the plate, but rather acts so as to apply a compound force that is directed in a diagonal direction across the body of the plate. The opening of the housing is elongated or slotted in the direction transverse to the axis of the slot so as to define linear angulation in the slot hole for the compression screw.

The plate also includes at least one slot 520 having a long axis, which is aligned with the direction of compression imposed by the compression screw. The slot receives a guide wire and allows it to remain in place stabilizing the bone fragments as the compression screw is tightened and a first bone segment is compressed against a second bone fragment. Optionally, the plate may include an additional guide wire hole 524 located in the vicinity of the compression housing. It is noted that the guide wire holes are smaller than the screw holes, and have a diameter that is slightly (i.e. between about 3 and 10% larger in diameter than, and preferably greater than about 3 and 7% larger than the diameter of a guide wire where the slotted version is from 1.5 to 3 times the diameter in length.) Alternatively as shown in FIG. 34, the slotted guide wire hole could be a slotted screw hole or compression hole 521 with a similar ratio of length to width (i.e. providing for a length that corresponds to the amount of compression that is achieved and is about 1-5 millimeters.) FIGS. 24-28 illustrate the plate 510 including plate screws 526 and compression screw 528. These views illustrate how the invention provides for the compression screw with a minimized concern for interference with the plate screws. FIG. 30 illustrates a threaded locking screw 600, that can be used with the invention, while FIG. 31 illustrates a compression screw 610, and FIG. 32 illustrates a variable locking screw assembly 620 that can be used with the present invention.

Figure 29:
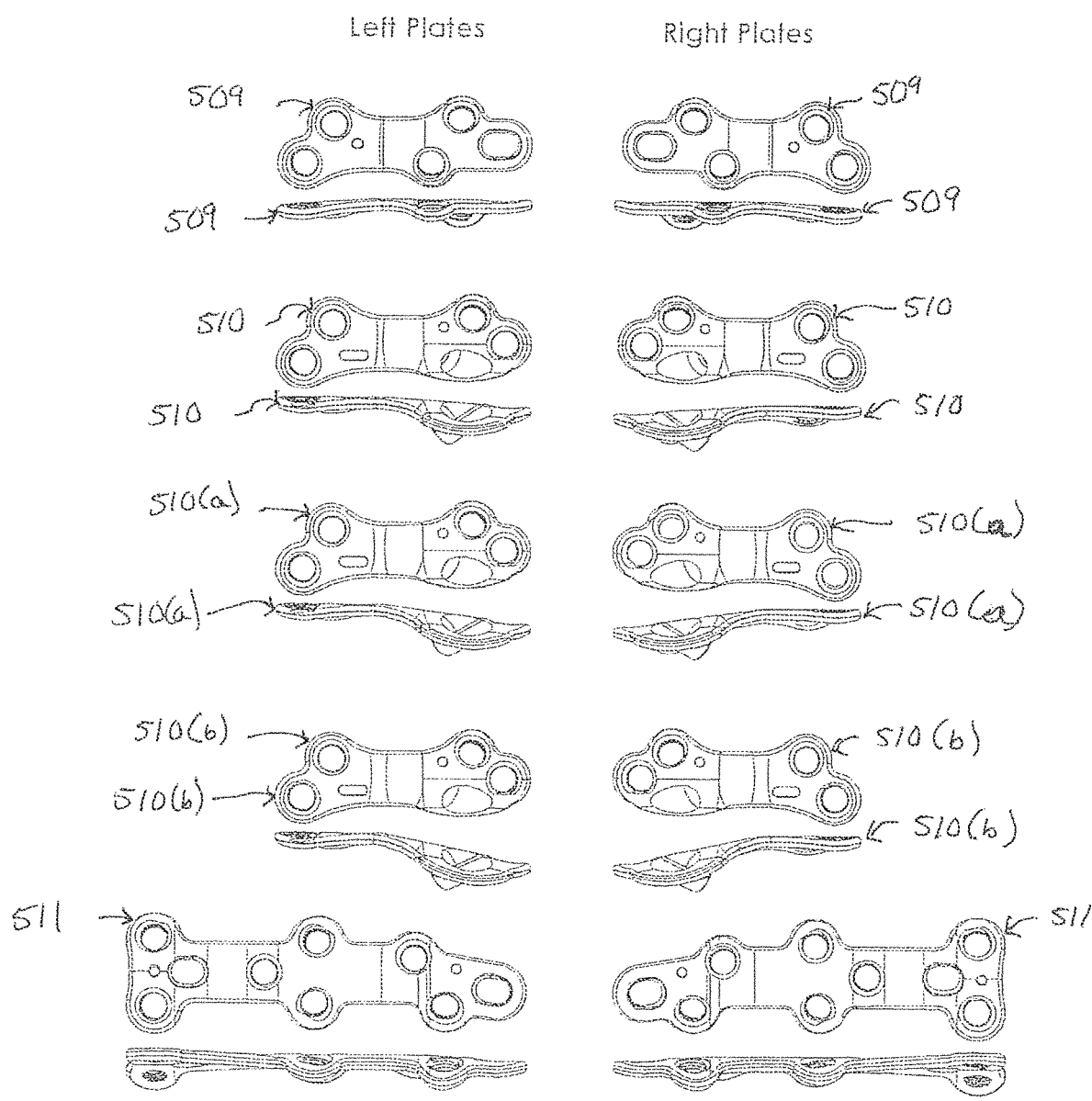
FIG. 29 is a view showing top and side views of a left and a right set of plates in accordance with a further embodiment of the invention.

The lapidus plate also includes mid-section 530 located intermediate the first and second ends and which can provide for an offset of varying degrees. Thus, in the plate system shown in FIG. 29, the plates are shown with a varying degree of offset provided in the mid-section. A medial column plate 511 is also provided which includes two opposing compression slots that act in opposition to each other, and which are provided in the distal and proximal ends of the plate. The system includes left and right versions of a non-pocketed plate 509; a neutral plate 510; a 4° correction plate 510(a); a 8° correction plate 510 (b) and the medial column plate 511.

In one method of causing locking of the screw relative to the plate, the screw 600 could include external screw threads 602 that mate with internal threads in the locking screw hole at a pre-selected angle, in some instances, the screw axis is perpendicular to a tangent at the top of the screw hole so that the screw axis angles slightly toward the bottom of the plate. However, other methods of causing locking could be employed, such as a variable locking assembly 622. The screw 610 used in the compression housing has a rounded rear shoulder 612 (such as a hemisphere, or a torroid), which allows for play in the convexly rounded recess in the compression housing. The compression is caused when the compression screw engages the bone and pulls the plate into that bone as it engages a downwardly sloping shoulder on the compression slot, and the locking screw or screws act on their respective bone segment.

The screws shown in FIGS. 30-32 which are useful with the plate of the present invention are self-starting, self-tapping screws including the option of partial or full cannulation. The screws include a cutting end having multiple flutes, and preferably 2 or 3 flutes about a conical recess, and preferably have a rounded end to avoid soft tissue irritation should they break an opposing cortical surface. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.2 and 1.5 millimeters, and most preferably between about 1.25 and 1.40 millimeters. The compression housing extends a depth below the bottom surface of the plate from about 1.4 to about 3 mm, preferably from about 1.75 to about 2.25 mm, and has a width of from about 3.5 to about 5.5, preferably from about 4 to about 5 mm, and a length of from about 3.0 to about 8.0, mm preferably from about 5.0 to about 7.0 mm. The opening in the upper surface of the plate for the compression opening is from about 8 to about 15 mm in width, and from about 10 to about 18 mm in length. The lower opening is about 2.5 to about 2.9 mm in diameter with a recess width of from about 2.5 to about 4.5 mm. The locking screw holes include a flat annular recess surrounding the threaded area that is about 0.4 to about 0.6 mm in width. The universal plate (i.e. the tab-like plate) has a length of from about 35 to about 45 mm, preferably from about 38 to about 42 mm, and the compression screw axis forms an angle of from about 30° to about 40° to a longitudinal axis on the top of the plate. The MTP plate has a length of from about 40 to about 50 mm in length. The compression screw axis forms an angle of about 22° to about 37° with a longitudinal axis tangent to the bottom of the plate at the housing exit. In the bunionectomy plate, the chamfer at the bone insertion end is from about 5° to about 15°, preferably from about 8° to about 12°, and the length of the chamfer is from about 2 to about 4 mm, preferably from about 2.5 to about 3.5 mm and the plate has a total length of from about 175 to about 225 mm, preferably from about 185 to about 200 mm, with the taper. The axis of the compression screw forms an angle of from about 35° to about 45° to a longitudinal axis on the bottom of the plate. The plate includes a continuous outer edge, which is defined between the top and the bottom surface. In addition, the plate can include a small through hole sized to receive a K-wire or othersimilar guide wire.

During the surgery the joints are first prepped which may include de-articulation between the bones to be fused. The bones are reduced, the plate is located such that all of the screws are aimed into the targeted bones and away from the joint, and the locking screw(s) is inserted into a pre-drilled pilot hole or holes. A pilot hole is drilled for the compression screw, and the compression screw is tightened into position. The two locking screws are screwed into adjacent cunieforms. The plate is viewed radiographically. The incision is closed per the usual method.

The following is a description of a surgical technique for an MTP fusion using the MTP fusion plate in accordance with the present invention. First, prepare the MTP joint for fusion and choose the desired plate from the surgical tray. Note, that the plates are pre-contoured to provide 10° of valgus and 5° of dorsiflexion and can be used on either foot. The plates should be placed so that the plate's pocket is on the medial side of the foot. For instance, using the Alpha™ plate on the right foot the pocket is on the proximal side of the joint. When used on the left foot, the pocket of the Alpha™ plate is on the distal side of the joint. If necessary, use the bending pliers to contour the plate to the bone surface. Using a k-wire, placed in the plantar portion of the bones from medial to lateral across the joint, temporarily fix the joint in the desired position. Assemble the template that corresponds to the chosen plate with the countersink guide by snapping the template into the guide. Lay the template on the bone and orient to the desired position of the plate. Place two 0.9 mm k-wires. Prepare for the plate pocket and inter-fragmentary screw with the provided countersink through the template assembly. Insert the countersink until the shoulder of the countersink hits the guide normal to the plate in the k-wire holes. With the k-wires still in place, slide the template off the bone and using the wires to help placement, slide the chosen plate over the k-wires so that the plate's pocket fits within the prepared hole. Select one of a fixed locking, non-locking or variable angle locking screw to be used in one of the threaded locking holes that is on the same side of the joint, proximally or distally, as the pocket and chose the appropriate drill bit based on the screw selection. Using a color-coded drill guide, drill to the desired depth, determine the screw length using the depth gages, and insert a selected screw into the hole and drive the screw for each screw hole. Using the 1.4 mm guide wire tip, insert a 1.4 mm guide wire in to the pocket hole across the MTP joint and ensure that the guide tip is seated within the pocket before inserting the wire. Use the cannulated drill bit to drill for the inter-fragmentary pocket screw over the guide wire. Determine the required screw length over the guide wire using the depth gage and insert the inter-fragmentary screw in the pocket of the plate using the corresponding driver. Before the pocket screw is completely seated, remove the k-wire used for temporary fixation and fully tighten the pocket screw. Fill all remaining screw holes and completely tighten all remaining screws. Verify the correct placement of the plate and screws, replace soft tissue and close the opening.

The present invention offers a site-specific design for fixation and fusions involving the first metatarsocuneiform (MTC) joint. The system includes several plates for varying degrees of deformity correction, from neutral (no correction) to 8° past neutral. All plates feature an anatomically contoured design to fit the medial aspect of the joint. The implant design allows the plate to fit the flatter cuneiform and curved first metatarsal, creating a low-profile construct and reducing the need for intra-operative plate bending. The present invention allows insertion of a targeted 4.0 mm inter-fragmentary screw through the plate, designed to maximize compression and reduce the risk of hardware collision associated with supplementary cross-screw insertion outside of a plate. The system further allows the plates to accommodate all of non-locking, fixed-angle locking and variable-angle locking screws for fixation without compromise. The compression screw can be a partially threaded or fully threaded cannulated or solid screw. All of these can be provided in the surgical tray or caddy and thus are made available at the time of surgery.

The steps of the surgery are detailed below:

Step 1: Perform standard exposure and prepare the metatarsocuneiform (MTC) joint according to surgeon preferred technique for a medial approach.

Figure 33A:
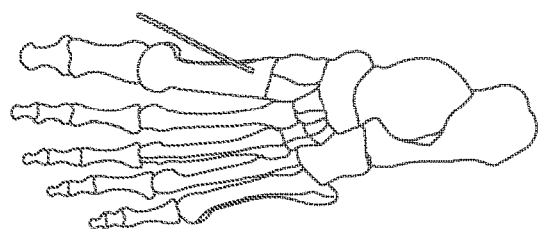
FIG. 33(a)-33(l) illustrates a method of performing a surgery using the plates and instruments in accordance with the invention.

Step 2: Temporarily fix the joint in the desired orientation using the provided k-wires. Recommended wire placement is through the dorsal aspect of the joint, directed into the plantar-lateral aspect of the cuneiform and into the intermediate cuneiform or second metatarsal if desired. FIG. 33(a).

Step 3: Select the plate template. The plate and templates are side specific and designed so that the pocket is on the plantar-medial aspect of the joint and a template is provided at each offset corresponding to the appropriate degree of correction: i.e. neutral (0° of correction), 4° past neutral, and 8° past neutral. Note that the neutral template has a slight bend to fit the natural angle of the joint. The 4° and 8° designations reflect the amount of bend past neutral and do not necessarily correspond to the total IM correction angle.

Figure 33B:
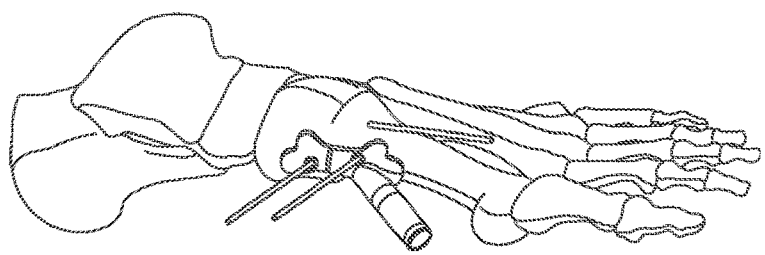
Figure 33C:
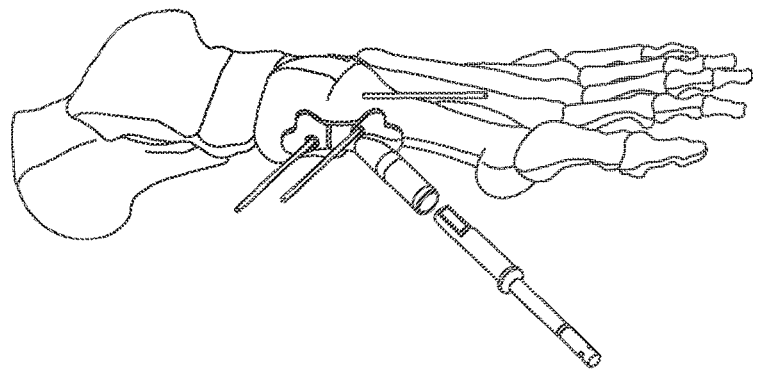

Step 4: Insert a 1.4 mm k-wire through each k-wire hole in the template. The templates include raised nubs which surround the guide wire holes in order to provide for parallel placement of the guides wires relative to each other, and an alignment that is desired relative to the foot. Take care to keep the wires parallel during insertion as they will later facilitate plate placement. FIG. 33(b).

Figure 33D:
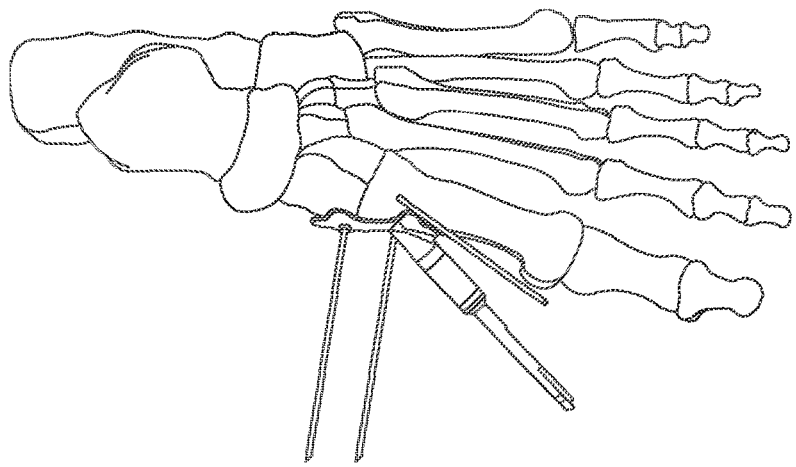

Step 5: Select the provided countersink and drill through the template to prepare a pocket for the plate. FIG. 33 (c). Ensure that the template is held tightly against the bone during this step in order to fully prepare the pocket. Insert the countersink until the shoulder of the countersink hits the guide. FIG. 33(d).

Figure 33E:
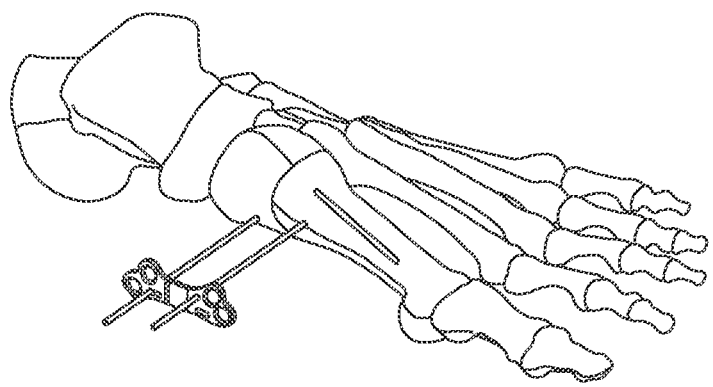
Figure 33F:
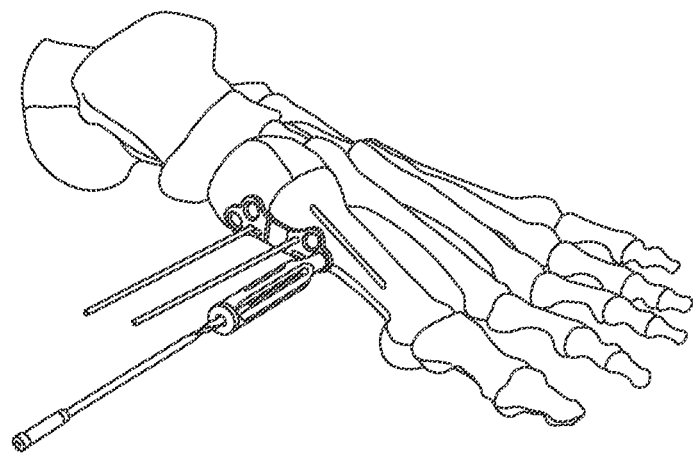

Step 6: With the k-wires still in place, slide the template off the bone. Then slide the corresponding plate over the wires and position into the prepared pocket. FIG. 33(e). The proximal k-wire should pass through the k-wire slot in the plate. Step 7: Using the fixed drill guide and the 2.4 mm drill bit, drill a pilot hole for the most distal screw. FIG. 33(f). Take care to not move the plate after drilling for a locking screw in order to maintain the proper pilot hole alignment and prevent locking screw cross-threading. The threaded screw holes in the plate are compatible with a variety of screw options; 3.5 mm non-locking or fixed-angle locking screws (magenta) and 4.0 mm non-locking screws (teal) are included in the Set. Depending on surgeon preference, a combination of screw types can be used.

Step 8: Determine the screw length required using the provided depth gage.

Step 9: Remove the desired screw from the screw caddy using the provided driver. For all screws used throughout the procedure, verify the screw length using the gauge provided on the screw caddy.

Step 10: With the driver, insert the selected screw into the hole and drive the screw.

Step 11: Follow the same technique for the remaining distal screw hole.

Step 12: Select the 1.4 mm pocket wire guide and place the nose into the plate pocket, aligning the solid line on the guide with the dashed line on the plate.

Figure 33G:
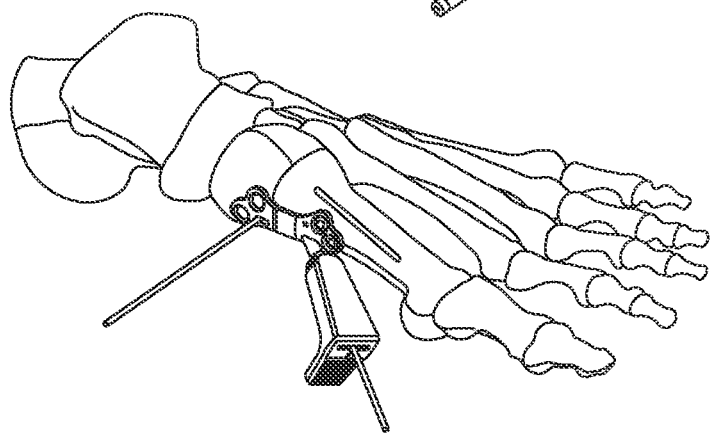

Step 13: With the guide fully seated in the plate pocket, insert a 1.4 mm guide wire through the guide at the desired trajectory. FIG. 33(g). The recess within the pocket wire guide is slotted to allow for 12° of planar angulation within the slot of the compression housing. Verify wire placement with fluoroscopy to ensure trajectory and screw purchase will be adequate.

Figure 33H:
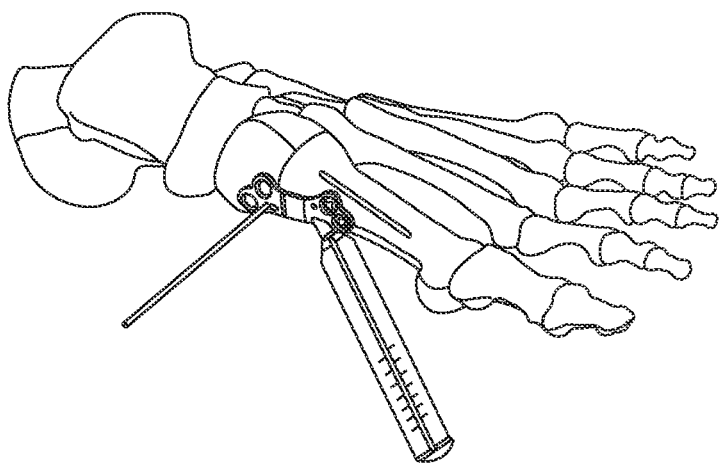

Step 14: Remove the pocket wire guide and use the provided pocket depth gauge to measure over the wire and determine the required screw length. Keep in mind that a shorter screw may be required based on compression generation. FIG. 33(h).

Step 15: Use the cannulated drill bit to drill over the wire for the 4.0 mm pocket screw.

Figure 33I:
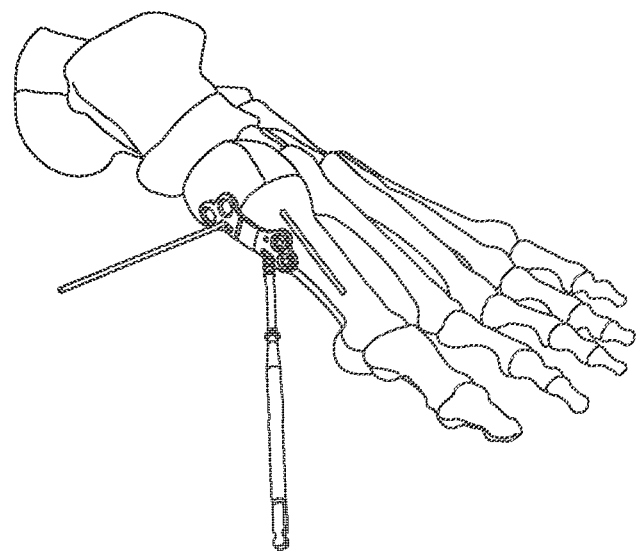
Figure 33J:
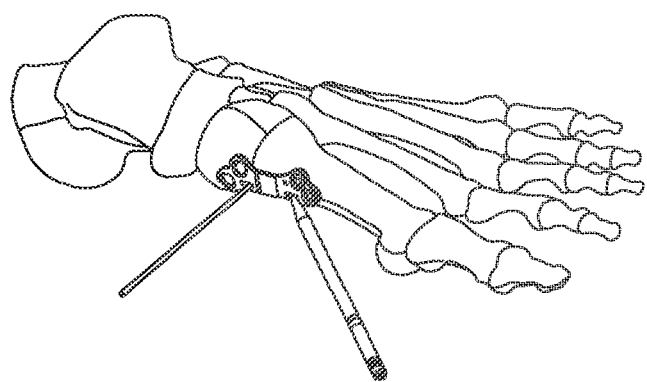

Step 16: Remove the 1.4 mm guide wire from the pocket in order to insert a partially threaded solid screw. Leave any other provisional fixation in place to maintain proper alignment. FIG. 33(i). If a cannulated screw is used the pocket guide wire may be left in place during initial screw insertion to further maintain joint alignment.

Step 17: Using the driver, insert the appropriate length partially threaded screw through the pocket until almost fully seated in the pocket. FIG. 33O).

Step 18: Remove any provisional fixation wires and fully tighten the pocket screw. The proximal k-wire may remain in place during screw insertion to maintain plate alignment; the slot will allow plate translation during pocket screw insertion.

Figure 33K:
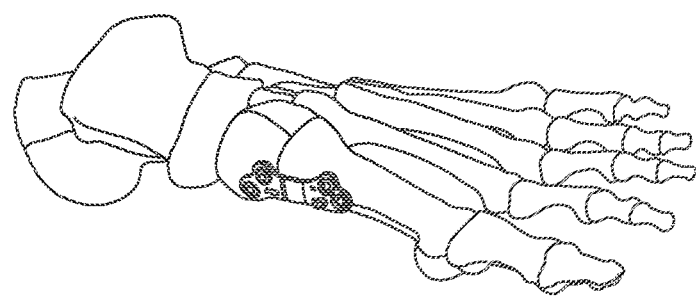
Figure 33L:
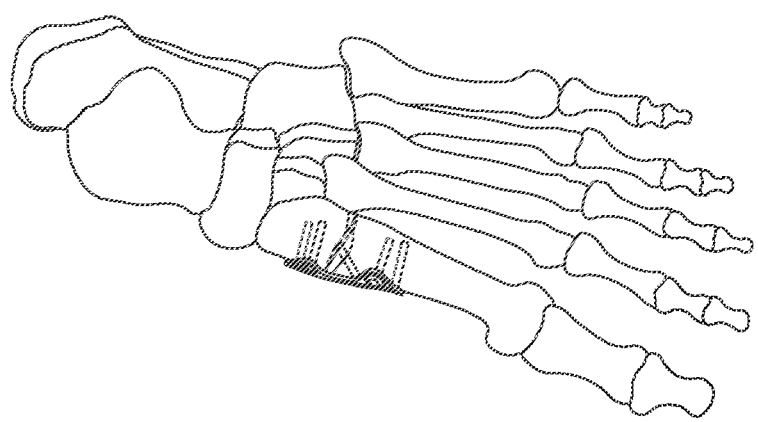

Step 19: Remove all remaining wires. Drill and insert the proximal screws using the technique described in Steps 8-10 above. Fully tighten all screws. FIG. 33(k). Verify final plate and screw placement with fluoroscopy to ensure correct joint. FIG. 33(l).

While in accordance with the patent statutes the best mode and preferred embodiment have been set forth, the scope of the invention is not limited thereto, but rather by the scope of the attached claims.

What is claimed is:

1. A plate, comprising:
  a body having a thickness extending between a top surface and an opposing bone facing surface, the body extending along a longitudinal axis between a first end and a second end that are offset by an angle between 2° and 14° wherein the first end has two tabs with each defining a locking hole and the second end has three lobes with each defining a locking hole and the second end further including a fourth lobe which defines a compression hole, wherein the body defines a medial line, wherein the first end includes a terminal portion defining at least one locking hole, wherein the body defines at least one guide wire slot having a width sufficient to accommodate a guide wire but not sufficient to accommodate either a compression screw or a locking screw, and a length greater than the width so as to be sized and configured to receive a guide wire therethrough; and
  a compression screw housing located at a position spaced apart from the first end and not located on the medial line, the compression screw housing extending from the bone facing surface of the body, wherein the compression screw housing defines a compression screw hole extending at a compression screw angle relative to the longitudinal axis at an angle substantially between about 20° to about 60° from the top surface through the compression screw housing, wherein the compression screw hole defines a groove in the top surface of the plate, wherein the compression screw hole is configured to receive either the compression screw or the locking screw therethrough, wherein the compression screw or the locking screw is configured to apply a compound compressive force to a first bone part when inserted through the compression screw hole in a diagonal direction across the body so as to provide interfragmentary bone compression, and wherein the guide wire slot has a length in the direction of the compression screw hole which is greater than a width of the guide wire slot.

2. A system, comprising:
  at least one locking screw having a first diameter and a first length;
  a compression screw having a second diameter and a second length, wherein the second diameter is greater than the first diameter and the second length is greater than the first length; and
  a plate comprising a top surface opposing a bone facing surface in a z direction, the plate extending along a first length along a longitudinal axis and having a body extending along the longitudinal axis and defining a first end and a second end that are offset by an angle between 2° and 14° wherein the first end has two tabs with each defining a locking hole and the second end has at least two lobes each defining a locking hole and a third lobe which defines a compression hole, the body defining a medial line, the first end having a terminal portion with a locking hole and the plate including a compression screw housing extending from the bone facing surface of the plate and located at a position spaced apart from the first end and not located on the medial line and defining a compression screw hole extending at a compression screw angle relative to the longitudinal axis of about 20° to about 60°, wherein the compression screw is configured to apply a compressive compound force to a first bone part when inserted through the compression screw hole in a diagonal direction across the body of the plate so as to provide interfragmentary bone compression.

3. A plate and screw system capable of fixation of bone comprising:

a plate, a locking screw, and a compression screw;

the plate having a body defining a first end and a second end that are offset by an angle between 2° and 14° wherein the first end has only two tabs with each defining a locking hole and the second end has three lobes with each defining a locking hole and the second end further including a fourth lobe which defines a compression hole with a top surface configured to oppose a bone facing surface, a locking hole defined adjacent to the first end a compression screw housing located at a position spaced apart from the first end and defining an angled compression screw hole extending at an angle relative to top surface that is less than 90°, the compression screw housing projecting from the bone facing surface wherein the compression screw is configured to apply a compound compressive force to a first bone part when inserted through the compression screw hole in a diagonal direction across the body of the plate so as to provide interfragmentary bone compression.

4. The plate and screw system as set forth in claim 3, wherein the compression screw angle is from about 30° to about 70°.

5. The plate and screw system as set forth in claim 4, wherein the compression screw angle is from about 20° to about 60°.

6. The plate and screw system as set forth in claim 3, wherein the compression screw housing is off-set in relation to an edge of the plate.

7. The plate and screw system as set forth in claim 3, further including a plurality of locking screws, and wherein the first end of the plate defines a plurality of tabs, each tab includes a threaded hole for one of the plurality of locking screws.

8. The plate and a screw system as set forth in claim 3, wherein the first end has three tabs with each defining a locking hole, and the second end defines two holes with each defining a locking hole, and the compression screw housing being located intermediate of the first end and the second end.

9. The plate and screw system as set forth in claim 3, wherein the plate further defines a slot having a width sufficient to accommodate a guide wire, and a length greater than the width.

* * * * *